(12) United States Patent
Doerr et al.

(10) Patent No.: US 10,258,283 B2
(45) Date of Patent: Apr. 16, 2019

(54) IMPLANT AND INSERTION DEVICE FOR AN IMPLANT

(71) Applicant: Biotronik SE & Co. KG, Berlin (DE)

(72) Inventors: Thomas Doerr, Berlin (DE); Michael Diebold, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 942 days.

(21) Appl. No.: 14/802,974

(22) Filed: Jul. 17, 2015

(65) Prior Publication Data

US 2016/0051194 A1 Feb. 25, 2016

Related U.S. Application Data

(60) Provisional application No. 62/038,844, filed on Aug. 19, 2014.

(51) Int. Cl.
| | |
|---|---|
| *A61B 5/00* | (2006.01) |
| *A61N 1/05* | (2006.01) |
| *A61L 24/00* | (2006.01) |
| *A61L 24/02* | (2006.01) |
| *A61L 24/06* | (2006.01) |
| *A61L 24/10* | (2006.01) |
| *A61N 1/372* | (2006.01) |
| *A61N 1/375* | (2006.01) |

(52) U.S. Cl.
CPC .......... *A61B 5/688* (2013.01); *A61L 24/0036* (2013.01); *A61L 24/02* (2013.01); *A61L 24/06* (2013.01); *A61L 24/10* (2013.01); *A61L 24/104* (2013.01); *A61L 24/106* (2013.01); *A61L 24/108* (2013.01); *A61N 1/05* (2013.01); *A61N 1/057* (2013.01); *A61N 1/059* (2013.01); *A61N 1/3756* (2013.01); *A61N 1/37205* (2013.01); *A61N 2001/058* (2013.01)

(58) Field of Classification Search
CPC .......... A61N 1/05; A61N 1/057; A61N 1/059; A61N 1/3756; A61N 1/37205; A61L 24/0036; A61B 5/688
USPC ...................................... 606/1, 377
See application file for complete search history.

(56) References Cited

U.S. PATENT DOCUMENTS

| | | | | |
|---|---|---|---|---|
| 5,209,776 | A | * | 5/1993 | Bass ................ A61B 17/00491 106/124.1 |
| 6,689,056 | B1 | | 2/2004 | Kilcoyne et al. |
| 2003/0055313 | A1 | * | 3/2003 | Anderson .......... A61B 17/0469 600/29 |
| 2005/0222537 | A1 | | 10/2005 | Dinsmoor et al. |
| 2006/0089690 | A1 | | 4/2006 | Gerber |
| 2006/0247724 | A1 | | 11/2006 | Gerber et al. |
| 2007/0100387 | A1 | | 5/2007 | Gerber |
| 2010/0086529 | A1 | | 4/2010 | Mohammad et al. |

(Continued)

OTHER PUBLICATIONS

European Search Report received from EP Application Serial No. 17182247.1, dated Nov. 28, 2017, 6 pages.

(Continued)

*Primary Examiner* — Nathan J Jenness
(74) *Attorney, Agent, or Firm* — Arc IP LAW, PC; Joseph J. Mayo

(57) ABSTRACT

Embodiments include an implant for insertion into a human and/or animal body and an insertion device for the implant. The implant includes a housing, at least one negative pressure unit and at least one adhesive application unit to temporarily and/or permanently fix the implant to a bodily tissue.

14 Claims, 5 Drawing Sheets

(56) References Cited

U.S. PATENT DOCUMENTS

| | | |
|---|---|---|
| 2010/0114285 A1 | 5/2010 | Aron et al. |
| 2012/0041338 A1 | 2/2012 | Chickering, III et al. |
| 2012/0245663 A1* | 9/2012 | Zarembo .................. A61N 1/05 607/116 |
| 2013/0013044 A1 | 1/2013 | Thacker et al. |

OTHER PUBLICATIONS

European Search Report received from EP Application Serial No. 15168075, dated Jan. 13, 2016, 6 pages.

\* cited by examiner

IMPLANT AND INSERTION DEVICE FOR AN IMPLANT

This application claims the benefit of U.S. Provisional Patent Application 62/038,844 filed on 19 Aug. 2014, the specification of which is hereby incorporated herein by reference.

BACKGROUND OF THE INVENTION

Field of the Invention

Embodiments of the invention generally relate to an implant and an insertion device for the implant.

Description of the Related Art

Generally, medical implants for insertion into the human or animal body are known. Some implants are typically intended to be temporarily or permanently fixed to bodily tissue area for diagnosis purposes and/or for therapy purposes.

For example, United States Patent Application 20060089690, to Gerber, entitled "Fixation of a Medical Implant to the Exterior of a Body Organ" appears to describe a laparoscopic method for securing an implant. According to Gerber, some of the bodily tissue is sucked into a cavity of the implant by means of vacuum. As discussed in Gerber, a mechanical perforation is then made, and a fixing device is introduced, whereby the implant is permanently secured to the bodily tissue.

Generally, a perforation, such as the perforation introduced in Gerber, stresses the tissue and poses a risk of injury.

BRIEF SUMMARY OF THE INVENTION

One or more embodiments of the invention provide an implant that may be secured, temporarily or permanently, to bodily tissue in a manner that is gentle on tissue.

At least one embodiment of the invention provides an insertion device for such an implant.

One or more embodiments of the invention are achieved in accordance with the elements of the independent claims. Embodiments of the invention will emerge from the other claims, the description and the drawings presented herein.

At least one embodiment includes an implant that may be inserted into a human and/or animal body. In one or more embodiments, the implant includes a housing, at least one negative pressure unit, and an adhesive application unit to temporarily and/or permanently fix the implant to a bodily tissue.

In at least one embodiment, the implant may be positioned and fixed on a tissue surface, and initially fixed temporarily using negative pressure and then permanently fixed using an adhesive, without having to perforate the tissue surface during this process. In one or more embodiments, the implant may be positioned on a surface that is not directly visible and on moving bodily tissues. The area in which the negative pressure is applied, in at least one embodiment, may be the same area in which the adhesive is applied.

Embodiments of the invention relate to all implants that are to be fixed to bodily tissues. In at least one embodiment, the adhesive may include a biocompatible adhesive. According to one or more embodiments, materials may be used that either occur naturally in the body or that cannot be absorbed or metabolized by the human or animal organism, as biocompatible materials.

By way of at least one embodiment, a complication risk resulting with a tissue perforation may be avoided. For example, in one or more embodiments, complications such as a bleeding and infection risk and functional limitations, such as fibrosis, kinetic limitations or ectopic excitations in nerve or myocardial tissue may be avoided or at least reduced. Embodiments of the invention may be applied in regions with heavy circulation or in the case of blood vessels, such as when the implantation site is not visible during the implantation.

In at least one embodiment, the housing may include an adhesive surface to adhesively bond with the bodily tissue on a contact side of the implant or housing that may contact the bodily tissue. In one or more embodiments, the adhesive surface may include an adhesion-promoting structure, such as a porous structure. Such structures, in at least one embodiment, may include for example porous polyethylene, and may cause a particularly good adhesion of the adhesive.

At least one embodiment of the invention may include one or more sealing lips on the contact side of the implant or housing to locally delimit an adhesive spread. In one or more embodiments, the sealing lips may enclose the area of spread. In at least one embodiment, the adhesive may be kept away from sensor and/or electrode surfaces on the implant, which are provided on the side of the implant in contact with the bodily tissue. In one or more embodiments, a sealing function of the sealing lips may be checked by applying negative pressure when overlap exists between the areas in which the negative pressure and the adhesive are applied.

In at least one embodiment, the negative pressure unit may be formed as or may include a vacuum hose. In one or more embodiments, the vacuum hose may be detachable from, or detachably coupled to, the implant. In at least one embodiment, the vacuum hose that applies the negative pressure may remain in the body for a period of time following the fixing of the implant, and may be removed at later period of time non-invasively. At least one embodiment may include a removal aid that may be attached, for example a thread or the like, which may be operated externally.

In at least one embodiment, the negative pressure unit may be integrated in the implant as an evacuatable or evacuated negative pressure reservoir. In one or more embodiments, the negative pressure reservoir may be evacuated outside the body and then opened at the implantation site.

In at least one embodiment, the negative pressure unit may be coupled to the adhesive application unit such that a negative pressure selectively causes an adhesive release. In one or more embodiments, the adhesive release may be started and controlled by the negative pressure, for example when a closure membrane of the adhesive application unit opens from a defined negative pressure and releases the adhesive. If the adhesive distribution is caused by the negative pressure, one or more embodiments may include, on the basis of the pressure and/or volume curve, simultaneous detection of whether the adhesive bonding process is complete, for example when all provided channels and/or cavities are filled and closed with the adhesive.

In at least one embodiment, the adhesive application unit may deliver at least one component, as an adhesive or as a starting material for the adhesive, selected from one or more of glycoprotein, such as fibrinogen, 2-octyl-cyanoacrylate, and cross-linked gelatin. In one or more embodiments, the component applied by the adhesive application unit as an adhesive or as a starting material for the adhesive may be a base structure that forms a thrombus.

In at least one embodiment, the adhesive may include or may be formed from at least two main constituents, wherein one of the main constituents may be a glycoprotein, such as fibrinogen, and/or a protease inhibitor, such as aprotinin, and another of the main constituents may be thrombin and/or calcium chloride. According to one or more embodiments, one main constituent of the adhesive may be a base structure that forms a thrombus, and another main constituent may be one or more cross-linking additives, such as thrombin and/or factor XIII. In at least one embodiment, factor XIII, similarly to fibrinogen itself, is a coagulation factor. In one or more embodiments, the coagulation factor may act in the coagulation chain after fibrinogen or acts on converted fibrinogen, such as fibrin.

In at least one embodiment, the adhesive may include a fibrin adhesive foam that may easily be applied.

In at least one embodiment, the adhesive application unit may include a mixing element to mix adhesive components. In one or more embodiments of the invention that include an adhesive formed from a number of constituents, such as a fibrin adhesive, the implant may include a mixer to mix the constituents, such that the constituents are mixed only just before the release. As such, in at least one embodiment, the reliability of the adhesive bond is increased.

In at least one embodiment, the implant may include or may be formed as a pulse generator, a diagnostic sensor or an electrode line. One or more embodiments of the invention may be used with all implants that are to be fixed to bodily tissues.

At least one embodiment of the invention may include an insertion device for an implant, wherein the implant may be inserted into a human and/or animal body. In one or more embodiments, the implant may include a housing, at least one negative pressure unit, and an adhesive application unit to temporarily and/or permanently fix the implant to a bodily tissue. In at least one embodiment, the implant may be fixed to the insertion device and detached from the insertion device using negative pressure, when the negative pressure may be switched over to the negative pressure unit of the implant. By way of one or more embodiments, the negative pressure may be diverted by the actuation of a valve to the negative pressure unit of the implant.

At least one embodiment may include a negative pressure sensor. In one or more embodiments, the negative pressure sensor may be used to detect the correct placement of the implant and to check the adhesive bond. As such, in at least one embodiment, the adhesive release may be started and controlled by the negative pressure, for example when a closure membrane of the adhesive application unit opens from a defined negative pressure and releases the adhesive. If the adhesive distribution is caused by the negative pressure, one or more embodiments may include, on the basis of the pressure and/or volume curve, simultaneous detection of whether the adhesive process is complete, for example when all provided channels and/or cavities are filled and closed with the adhesive.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1A:
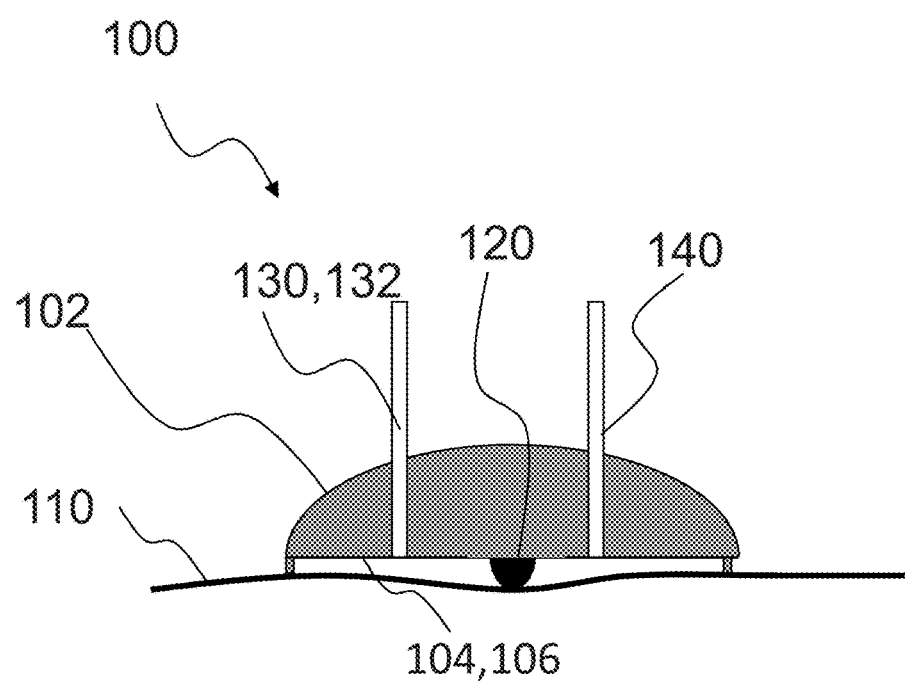
FIG. 1A schematically shows a section through an embodiment of an implant prior to the fixing to the bodily tissue with a vacuum line.
Figure 1B:
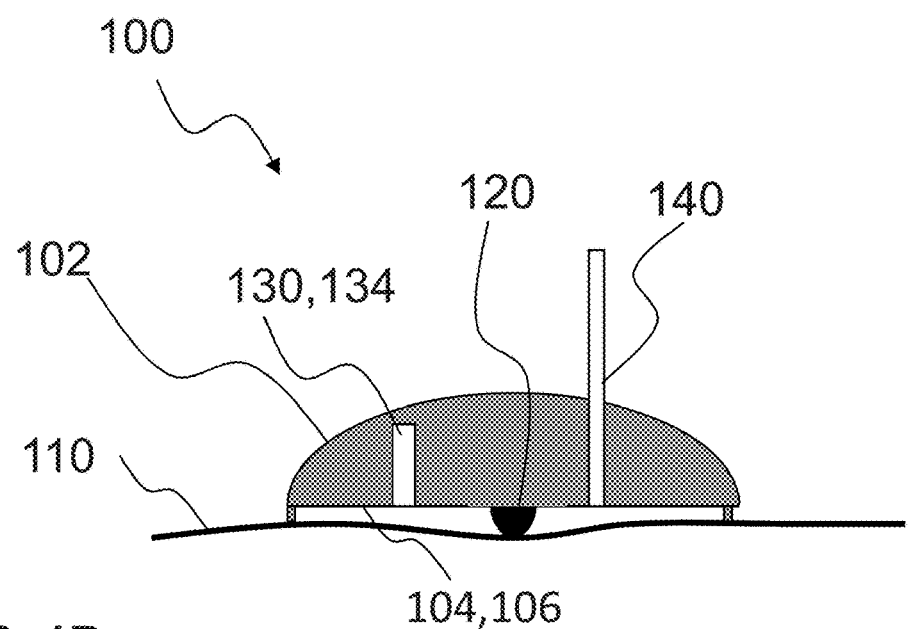
FIG. 1B schematically shows a section through an embodiment of an implant prior to the fixing to the bodily tissue with a negative pressure reservoir.

FIGS. 1A and 1B, according to one or more embodiments of the invention, each show an implant 100 that may be inserted into a human and/or animal body. In at least one embodiment, the implant 100 may include a housing 102, at least one negative pressure unit 130 and at least one adhesive application unit 140 to temporarily and/or permanently fix the the implant 100 to a bodily tissue 110. In one or more embodiments, the implant 100 may be a permanently implantable medical device, which may be fixed to a bodily tissue. In at least one embodiment, the implant 100 may include at least the negative pressure unit 130 to temporarily fix to the bodily tissue, which may fix the implant 100 to the bodily tissue via an introduced negative pressure. In one or more embodiments, the implant 100 may include at least the adhesive application unit 140 to apply one or more biocompatible adhesives, for example during the prevailing negative pressure fixing.

In at least one embodiment, the implant 100 may include at least one therapy or sensor unit 120 on the housing 102 that may be in contact with the bodily tissue 110.

In one or more embodiments, the housing 102 includes a housing underside, wherein the housing underside includes side 104 of the implant 100 that may be in contact with the bodily tissue 110. In at least one embodiment, the housing underside may include an adhesive surface 106 to adhesively bond, for example, with the bodily tissue. In one or more embodiments, the adhesive surface 106 may include an adhesion-promoting structure, such as a porous structure, to which the adhesive bonds to well.

During the negative pressure fixing, at least one embodiment may include a temporary testing of the implant functions. If a malfunction is determined, in one or more embodiments, the negative pressure may be removed and the implant 100 may be replaced. If, during the testing, it is revealed that the implant 100 is not correctly placed, at least one embodiment may include interrupting the negative pressure, shifting the implant 100 and reapplying the negative pressure to correctly place the implant 100.

In one or more embodiments, the negative pressure unit 130 may include a tubular line 132 (as shown in FIG. 1A), which ends in a cavity on the housing underside. In one or more embodiments, the other end of the tubular line 132 may include a device that enables evacuation, such as a syringe, or a suitable pump.

FIG. 1B schematically illustrates, according to at least one embodiment, a negative pressure reservoir 134 instead of the vacuum hose 132. In one or more embodiments, the negative pressure reservoir 134 may be evacuated externally outside the body and may be opened at the implantation site.

Figure 2A:
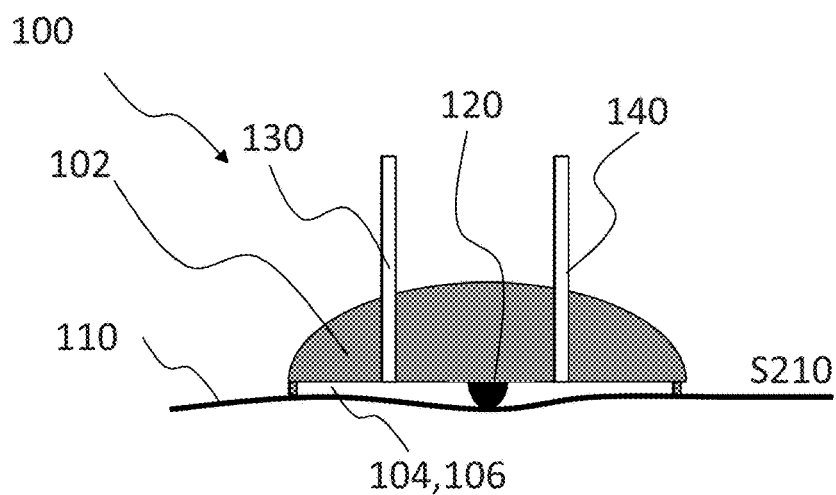
FIGS. 2A-2C schematically show, in sectional view, three steps when fixing an implant.
Figure 2B:
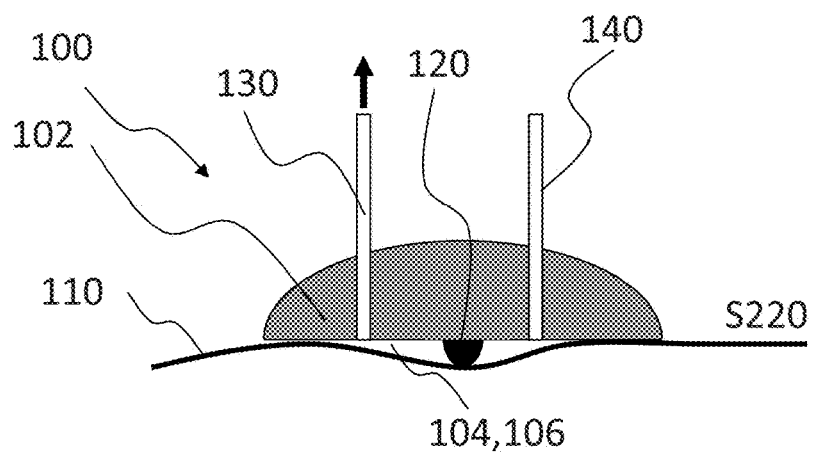
Figure 2C:
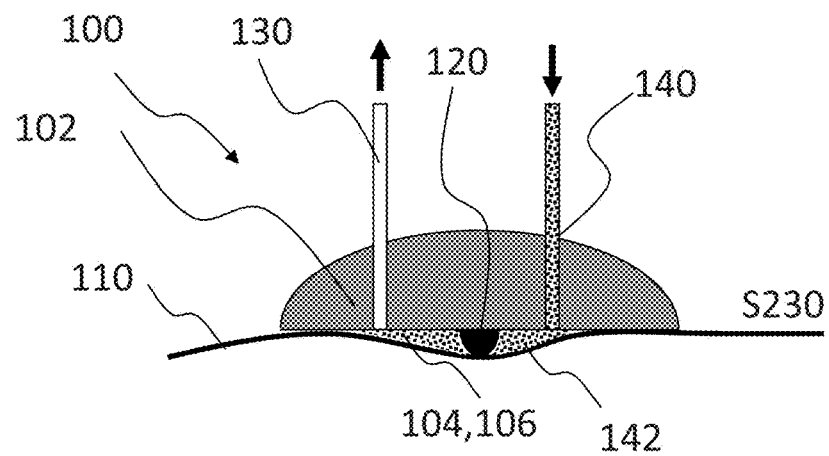

FIGS. 2A-2C show sectional views of three steps of fixing an implant 100, wherein an insertion device is not illustrated, according to one or more embodiments of the invention.

In a first step S210, by way of at least one embodiment, the implant 100 may be placed on the target tissue 110 using an insertion aid (not illustrated).

In a second step S220, by way of at least one embodiment, a negative pressure is produced at the housing underside, or the contact side 104, and as such the implant 100 may be temporarily fixed to the bodily tissue 110. In one or more embodiments, while being temporarily fixed, the implant 100 functions may be tested and the suitability of the site of implantation where the implant 100 is to be attached to may be tested. Should this test yield a negative result, in at least one embodiment, the implant 100 may be detached from the bodily tissue surface and repositioned in a residue-free and damage-free manner by reducing the negative pressure, as an advantage of the invention provided herein. In one or more embodiments, the temporary testing of implant functions in this state may be performed without the presence of the insertion aid, for example with implants 100 on moving bodily surfaces, such as the myocardium, as a further advantage of the invention provided herein, wherein the tests may be performed for the first time.

If the testing yields a positive result, by way of at least one embodiment, a biocompatible adhesive, such as fibrin adhesive, 2-octyl-cyanoacrylate or an alternative adhesive, for example a cross-linked gelatin, such as LifeSeal™ by Lifebond Israel, may be applied by the adhesive application device 140 in a third step S230 to ultimately fix the implant 100. In one or more embodiments, the adhesive may always be applied while maintaining the negative pressure in the region of the adhesive surface 106. As such, in at least one embodiment, the spread of the adhesive may be controlled or encouraged. In one or more embodiments, the negative pressure may be expediently maintained until the adhesive has cured sufficiently.

Figure 3:
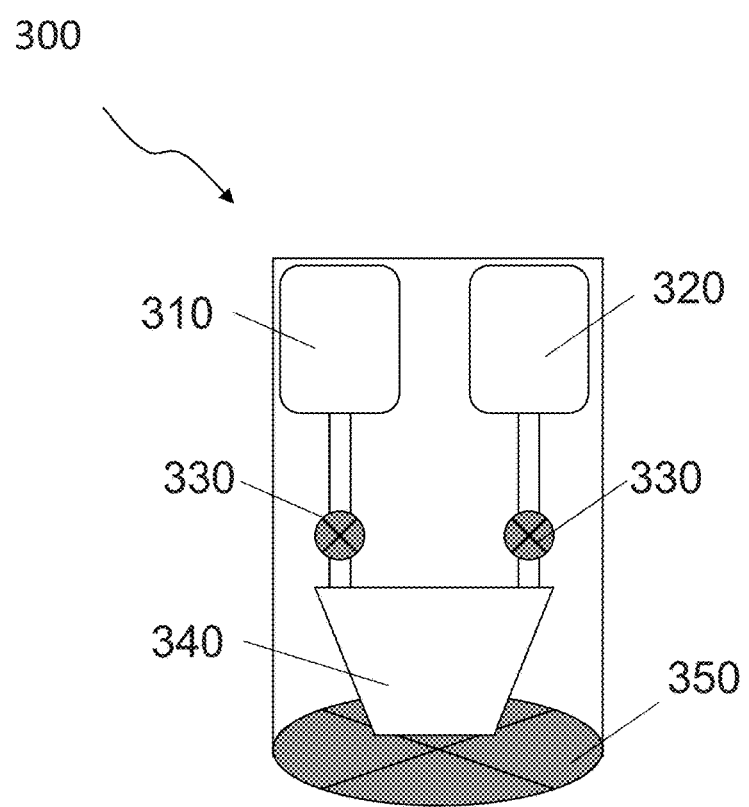
FIG. 3 schematically shows a device to apply an adhesive.

FIG. 3 shows a device to apply an adhesive according to one or more embodiments of the invention. Suitable fibrin adhesives, in at least one embodiment, may include two main components: a fibrinogen-containing component and a thrombin-containing component, wherein both may be used in liquid form.

In one or more embodiments, the suitable components of the fibrin adhesive may include, for example, fibrinogen or factor XIII as a first main constituent and thrombin as a second main constituent, or aprotinin as a first main constituent and calcium chloride as a second main constituent.

By way of at least one embodiment, thrombin and fibrinogen in the mixed state may cause the cleaving of the peptide chains of fibrinogen, such that the resultant fibrin polymerizes to form a coagulate or clump, which may be used to connect implant tissue and bodily tissue.

In order to avoid a premature coagulation, in one or more embodiments, the constituents of the fibrin adhesive should only be mixed at the site of action, wherein the two constituents must be kept separate until the actual adhesive bonding process.

At least one embodiment may include a device 300 that includes a plurality of separate adhesive constituent deposits, such as 310, 320, with two separate feed lines that correspond to the constituents of the fibrin adhesive. In one or more embodiments, the device 300 may include a mixing device 340 that mixes two or more constituents in the implant 100.

As shown in FIG. 3, one or more embodiments may include two release devices 330 that correspond to the adhesive constituents of the fibrin adhesive. In at least one embodiment, the two release devices 330 may be constructed such that they open at a defined pressure, wherein the defined pressure may be adjusted by the increase of the negative pressure, such that the adhesive process may be controlled very easily and advantageously via the control of the negative pressure.

Once the adhesive constituents have been released, by way of one or more embodiments, the adhesive constituents may be mixed in the mixing device 340 using a swirling principle and may then be released through a porous polymer adhesive target 350 into the cavity, affected by the negative pressure, between the implant 100 and bodily tissue 110. As such, in at least one embodiment, the implant 100 may be adhesively bonded to the target tissue.

By way of one or more embodiments, the device 300 may be used with all adhesive types. In at least one embodiment, device 300 may include a simpler structure, so that device 300 may be used together with adhesives having just one constituent.

Figure 4A:
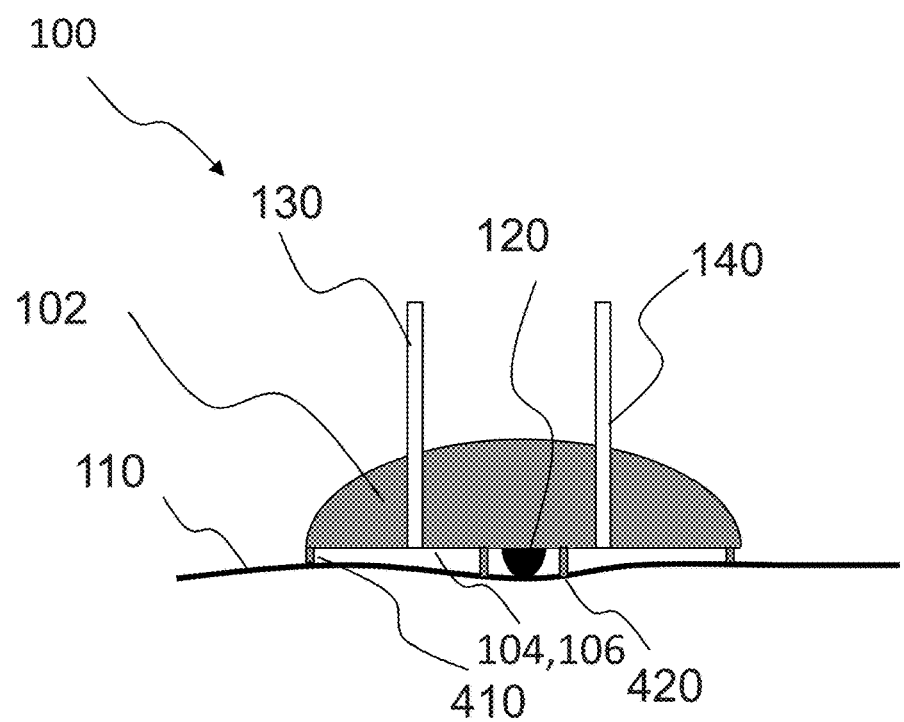
FIG. 4A schematically shows, in sectional view, sealing elements of an implant.
Figure 4B:
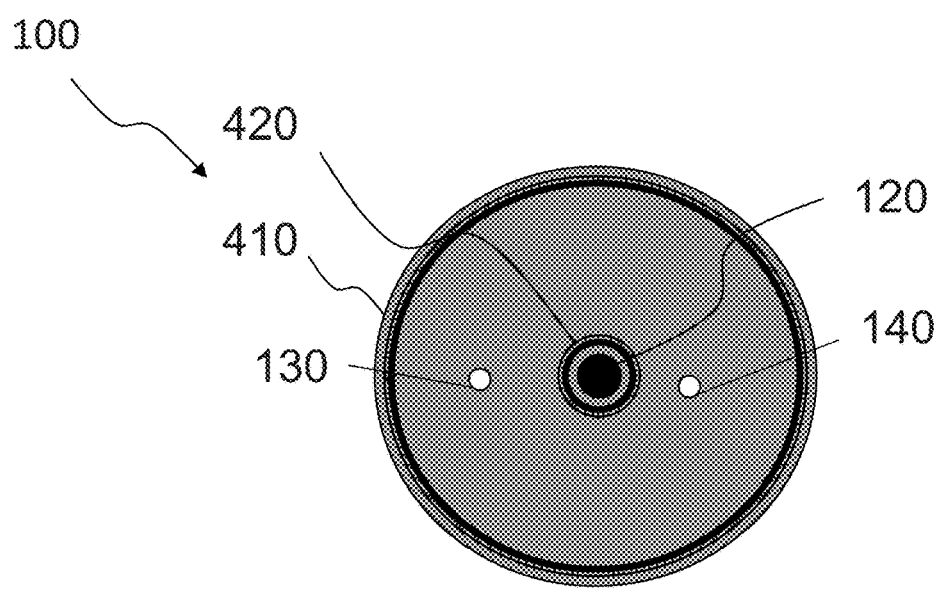
FIG. 4B schematically shows, in plan view, sealing elements of an implant.

FIGS. 4A and 4B, as a sectional view (FIG. 4A) and as a plan view (FIG. 4B), show the implant 100 with sealing elements 410, 420, for example sealing lips or sealing frames, according to one or more embodiments of the invention. In at least one embodiment, the outer sealing element 410 may prevent the spread of the adhesive outside of the implant 100, and the inner sealing element 420 may prevent the spread of the adhesive into the region in which the therapy or sensor element 120 is arranged. As such, in at least one embodiment, the function of the implant 100 remains unaffected by the adhesive. In one or more embodiments, the adhesive may spread only within the region delimited by the sealing elements 410, 420.

Figure 5:
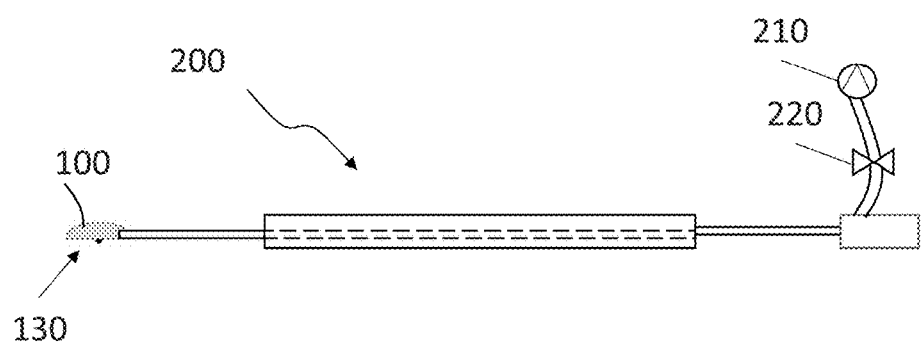
FIG. 5 schematically shows an insertion device with an implant in accordance with an embodiment of the invention.

FIG. 5 shows a simplified version of an insertion device 200, for example a laparoscopy, a catheter or the like, with an implant 100, according to at least one embodiment of the invention.

When the implant 100 is inserted, in one or more embodiments, the implant 100 may be held on the insertion device 200 using negative pressure. In at least one embodiment, the negative pressure may be provided by an external unit 210, for example a pump or the like. In one or more embodiments, a negative pressure unit 130 in the implant 100 may be connected to the unit 210. At least one embodiment of the invention may include a valve 220 at the proximal end of the insertion device 200, wherein the valve 220 may switch over the negative pressure between a holding device of the implant 100 on the insertion device 200 and the negative pressure unit 130 in the implant 100. In one or more embodiments, the implant 100 may detach from the insertion device 200 and may suction itself fixedly to the body tissue.

One or more embodiments of the invention include temporarily and permanently fixing an implant 100 to a tissue surface 110 without perforation thereof, to position the implant 100 at currently inaccessible implantation sites.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein.

Therefore, it is the intent to cover all such modifications and alternate embodiments as may come within the true scope of this invention.

What is claimed is:

1. An implant for insertion into a human and/or animal body, comprising:
    a housing;
    at least one negative pressure unit; and,
    at least one adhesive application unit configured to temporarily or permanently fix the implant to a bodily tissue,
    wherein the at least one negative pressure unit is coupled to the at least one adhesive application unit such that a negative pressure selectively causes an adhesive release.

2. The implant as claimed in claim 1, wherein the housing comprises
    a contact side configured to contact the bodily tissue, and
    an adhesive surface configured to adhesively bond to the bodily tissue.

3. The implant as claimed in claim 2, wherein the adhesive surface comprises an adhesion-promoting structure comprising a porous structure.

4. The implant as claimed in claim 2, wherein said contact side comprises one or more sealing elements to locally delimit an adhesive spread.

5. The implant as claimed in claim 1, wherein the at least one negative pressure unit comprises a vacuum hose.

6. The implant as claimed in claim 5, wherein the vacuum hose is detachably connected to the implant.

7. The implant as claimed in claim 1, wherein the at least one negative pressure unit is integrated in the implant as an evacuatable or evacuated negative pressure reservoir.

8. The implant as claimed in claim 1, wherein the at least one adhesive application unit delivers at least one component as an adhesive or as a staring material of an adhesive selected from glycoprotein, fibrinogen, 2-octyl-cyanoacrylate, and cross-linked gelatin.

9. The implant as claimed in claim 8, wherein the adhesive comprises at least two main constituents, wherein one of the at least two main constituents is one or more of a glycoprotein, fibrinogen, a protease inhibitor, aprotinin, and another of the at least two main constituents is one or more of thrombin and calcium chloride.

10. The implant as claimed in claim 8, wherein the adhesive comprises a fibrin adhesive foam.

11. The implant as claimed in claim 1, wherein the at least one adhesive application unit is coupled with a mixing device to mix adhesive components, wherein said mixing device is integrated in the implant.

12. The implant as claimed in claim 1, wherein said implant comprises a pulse generator, a diagnostic sensor or an electrode line.

13. A system for insertion into a human and/or animal body comprising:
    an implant, wherein the implant comprises:
        a housing,
        at least one negative pressure unit, and
        at least one adhesive application unit configured to temporarily or permanently fix the implant to a bodily tissue, wherein the at least one negative pressure unit is coupled to the at least one adhesive application unit such that a negative pressure selectively causes an adhesive release; and
    an insertion device, wherein the insertion device comprises:
        a holding device to hold the implant on the insertion device,
        an external negative pressure unit, and
        a valve;
    wherein the implant is fixed to the insertion device using negative pressure, and detached from the insertion device when the negative pressure of the external negative pressure unit is switched over from the holding device to the at least one negative pressure unit of the implant.

14. The system as claimed in claim 13, further comprising a negative pressure sensor, wherein the negative pressure sensor is part of the implant.

* * * * *